(12) United States Patent
Hernandez et al.

(10) Patent No.: US 8,120,369 B2
(45) Date of Patent: Feb. 21, 2012

(54) DIELECTRIC CHARACTERIZATION OF BITUMINOUS FROTH

(75) Inventors: Victor Hernandez, Merritt Island, FL (US); John White, Melbourne, FL (US)

(73) Assignee: Harris Corporation, Melbourne, FL (US)

( * ) Notice: Subject to any disclaimer, the term of this patent is extended or adjusted under 35 U.S.C. 154(b) by 451 days.

(21) Appl. No.: 12/395,953

(22) Filed: Mar. 2, 2009

(65) Prior Publication Data

US 2010/0219843 A1 Sep. 2, 2010

(51) Int. Cl.
*G01R 31/02* (2006.01)

(52) U.S. Cl. .................................................. 324/637

(58) Field of Classification Search .................. 324/637, 324/638, 642, 71.1
See application file for complete search history.

(56) References Cited

U.S. PATENT DOCUMENTS

| | | | |
|---|---|---|---|
| 2,371,459 A | 3/1945 | Mittelmann | |
| 2,685,930 A | 8/1954 | Albaugh | |
| 3,497,005 A | 2/1970 | Pelopsky | |
| 3,848,671 A | 11/1974 | Kern | |
| 3,944,910 A | 3/1976 | Rau | 324/6 |
| 3,954,140 A | 5/1976 | Hendrick | |
| 3,988,036 A | 10/1976 | Fisher | |
| 3,991,091 A | 11/1976 | Driscoll | |
| 4,035,282 A | 7/1977 | Stuchberry et al. | |
| 4,042,487 A | 8/1977 | Seguchi | |
| 4,087,781 A | 5/1978 | Grossi et al. | |
| 4,136,014 A | 1/1979 | Vermeulen | |
| 4,140,179 A | 2/1979 | Kasevich et al. | |
| 4,140,180 A | 2/1979 | Bridges et al. | |
| 4,144,935 A | 3/1979 | Bridges et al. | |
| 4,146,125 A | 3/1979 | Sanford et al. | |
| 4,196,329 A | 4/1980 | Rowland et al. | |
| 4,295,880 A | 10/1981 | Horner | |
| 4,300,219 A | 11/1981 | Joyal | |
| 4,301,865 A | 11/1981 | Kasevich et al. | |
| 4,328,324 A | 5/1982 | Kock | |
| 4,373,581 A | 2/1983 | Toellner | |
| 4,396,062 A | 8/1983 | Iskander | |
| 4,404,123 A | 9/1983 | Chu | |

(Continued)

FOREIGN PATENT DOCUMENTS

CA 1199573 A1 1/1986

(Continued)

OTHER PUBLICATIONS

"Oil sands." Wikipedia, the free encyclopedia. Retrieved from the Internet from: http://en.wikipedia.org/w/index.php?title=Oil_sands&printable=yes, Feb. 16, 2009.

(Continued)

*Primary Examiner* — Vincent Q Nguyen
(74) *Attorney, Agent, or Firm* — Allen, Dyer, Doppelt, Milbrath & Gilchrist, P.A.

(57) ABSTRACT

A method of determining a permittivity of a substance may include providing a probe having a planar end surface, providing a signal source and a signal receiver coupled to the probe, and physically contacting the substance with the planar end surface of the probe defining an interface. The method may further include measuring a reflection coefficient of the substance by at least transmitting a signal through the probe to the interface, receiving a reflected signal from the interface, and comparing the transmitted and reflected signals. The method may further include calculating the permittivity of the substance based upon the reflection coefficient.

13 Claims, 1 Drawing Sheet

U.S. PATENT DOCUMENTS

| | | | |
|---|---|---|---|
| 4,410,216 A | 10/1983 | Allen | |
| 4,425,227 A | 1/1984 | Smith | |
| 4,449,585 A | 5/1984 | Bridges et al. | |
| 4,456,065 A | 6/1984 | Heim | |
| 4,457,365 A | 7/1984 | Kasevich et al. | |
| 4,470,459 A | 9/1984 | Copland | |
| 4,485,869 A | 12/1984 | Sresty | |
| 4,487,257 A | 12/1984 | Dauphine | |
| 4,508,168 A | 4/1985 | Heeren | |
| 4,514,305 A | 4/1985 | Filby | |
| 4,524,827 A | 6/1985 | Bridges | |
| 4,531,468 A | 7/1985 | Simon | |
| 4,583,586 A | 4/1986 | Fujimoto et al. | |
| 4,620,593 A | 11/1986 | Haagensen | |
| 4,622,496 A | 11/1986 | Dattili | |
| 4,645,585 A | 2/1987 | White | |
| 4,678,034 A | 7/1987 | Eastlund | |
| 4,703,433 A | 10/1987 | Sharril | |
| 4,704,581 A | 11/1987 | Clark | 324/341 |
| 4,790,375 A | 12/1988 | Bridges | |
| 4,817,711 A | 4/1989 | Jeambey | |
| 4,882,984 A | 11/1989 | Eves, II | |
| 4,892,782 A | 1/1990 | Fisher et al. | |
| 5,046,559 A | 9/1991 | Glandt | |
| 5,055,180 A | 10/1991 | Klaila | |
| 5,065,819 A | 11/1991 | Kasevich | |
| 5,082,054 A | 1/1992 | Kiamanesh | |
| 5,136,249 A | 8/1992 | White | |
| 5,199,488 A | 4/1993 | Kasevich | |
| 5,233,306 A | 8/1993 | Misra | |
| 5,236,039 A | 8/1993 | Edelstein | |
| 5,251,700 A | 10/1993 | Nelson | |
| 5,293,936 A | 3/1994 | Bridges | |
| 5,304,767 A | 4/1994 | McGaffigan | |
| 5,315,561 A | 5/1994 | Grossi | |
| 5,370,477 A | 12/1994 | Bunin | |
| 5,378,879 A | 1/1995 | Monovoukas | |
| 5,506,592 A | 4/1996 | MacDonald | |
| 5,582,854 A | 12/1996 | Nosaka | |
| 5,621,844 A | 4/1997 | Bridges | |
| 5,631,562 A | 5/1997 | Cram | |
| 5,746,909 A | 5/1998 | Calta | |
| 5,910,287 A | 6/1999 | Cassin | |
| 5,923,299 A | 7/1999 | Brown et al. | |
| 6,045,648 A | 4/2000 | Palmgren et al. | |
| 6,046,464 A | 4/2000 | Schetzina | |
| 6,055,213 A | 4/2000 | Rubbo | |
| 6,063,338 A | 5/2000 | Pham | |
| 6,097,262 A | 8/2000 | Combellack | |
| 6,106,895 A | 8/2000 | Usuki | |
| 6,112,273 A | 8/2000 | Kau | |
| 6,184,427 B1 | 2/2001 | Klepfer | |
| 6,229,603 B1 | 5/2001 | Coassin | |
| 6,232,114 B1 | 5/2001 | Coassin | |
| 6,301,088 B1 | 10/2001 | Nakada | |
| 6,303,113 B1 | 10/2001 | Winter | |
| 6,348,679 B1 | 2/2002 | Ryan et al. | |
| 6,360,819 B1 | 3/2002 | Vinegar | |
| 6,432,365 B1 | 8/2002 | Levin | |
| 6,531,881 B1 * | 3/2003 | Cordes et al. | 324/644 |
| 6,603,309 B2 | 8/2003 | Forgang | |
| 6,613,678 B1 | 9/2003 | Sakaguchi | |
| 6,614,059 B1 | 9/2003 | Tsujimura | |
| 6,626,251 B1 | 9/2003 | Sullivan et al. | 175/40 |
| 6,649,888 B2 | 11/2003 | Ryan et al. | |
| 6,712,136 B2 | 3/2004 | de Rouffignac | |
| 6,808,935 B2 | 10/2004 | Levin | |
| 6,831,470 B2 * | 12/2004 | Xie et al. | 324/693 |
| 6,856,140 B2 * | 2/2005 | Talanov et al. | 324/638 |
| 6,886,632 B2 | 5/2005 | Raghuraman et al. | 166/252.4 |
| 6,923,273 B2 | 8/2005 | Terry | |
| 6,932,155 B2 | 8/2005 | Vinegar | |
| 6,967,589 B1 | 11/2005 | Peters | |
| 6,992,630 B2 | 1/2006 | Parsche | |
| 7,046,584 B2 | 5/2006 | Sorrells | |
| 7,079,081 B2 | 7/2006 | Parsche et al. | |
| 7,091,460 B2 | 8/2006 | Kinzer | |
| 7,109,457 B2 | 9/2006 | Kinzer | |
| 7,115,847 B2 | 10/2006 | Kinzer | |
| 7,147,057 B2 | 12/2006 | Steele | |
| 7,172,038 B2 | 2/2007 | Terry | |
| 7,205,947 B2 | 4/2007 | Parsche | |
| 7,312,428 B2 | 12/2007 | Kinzer | |
| 7,322,416 B2 | 1/2008 | Burris, II | |
| 7,337,980 B2 | 3/2008 | Schaedel | |
| 7,438,807 B2 | 10/2008 | Garner et al. | |
| 7,441,597 B2 | 10/2008 | Kasevich | |
| 7,461,693 B2 | 12/2008 | Considine et al. | |
| 7,484,561 B2 | 2/2009 | Bridges | |
| 7,562,708 B2 | 7/2009 | Cogliandro | |
| 7,623,804 B2 | 11/2009 | Sone | |
| 7,639,016 B2 | 12/2009 | Forgang | 324/358 |
| 7,665,355 B2 | 2/2010 | Zhang et al. | 73/152.48 |
| 7,752,906 B2 | 7/2010 | Pop et al. | 73/152.04 |
| 7,775,099 B2 | 8/2010 | Bogath et al. | 73/152.49 |
| 2002/0032534 A1 | 3/2002 | Regier | |
| 2004/0031731 A1 | 2/2004 | Honeycutt | |
| 2005/0199386 A1 | 9/2005 | Kinzer | |
| 2005/0274513 A1 | 12/2005 | Schultz | |
| 2006/0038083 A1 | 2/2006 | Criswell | |
| 2007/0108202 A1 | 5/2007 | Kinzer | |
| 2007/0131591 A1 | 6/2007 | Pringle | |
| 2007/0137852 A1 | 6/2007 | Considine et al. | |
| 2007/0137858 A1 | 6/2007 | Considine et al. | |
| 2007/0187089 A1 | 8/2007 | Bridges | |
| 2007/0261844 A1 | 11/2007 | Cogliandro et al. | |
| 2008/0073079 A1 | 3/2008 | Tranquilla | |
| 2008/0143330 A1 | 6/2008 | Madio | |
| 2009/0009410 A1 | 1/2009 | Dolgin et al. | |
| 2009/0242196 A1 | 10/2009 | Pao | |
| 2011/0140702 A1 | 6/2011 | Bloemenkamp | 324/355 |

FOREIGN PATENT DOCUMENTS

| | | |
|---|---|---|
| CA | 2678473 | 8/2009 |
| DE | 10 2008 022176 A1 | 11/2009 |
| EP | 0 135 966 | 4/1985 |
| EP | 0418117 A1 | 3/1991 |
| EP | 0563999 A2 | 10/1993 |
| EP | 1106672 A1 | 6/2001 |
| FR | 1586066 A | 2/1970 |
| FR | 2925519 A1 | 6/2009 |
| JP | 56050119 A | 5/1981 |
| JP | 2246502 A | 10/1990 |
| WO | WO 2007/133461 | 11/2007 |
| WO | 2008/011412 A2 | 1/2008 |
| WO | WO 2008/030337 | 3/2008 |
| WO | WO2008098850 A1 | 8/2008 |
| WO | WO2009027262 A1 | 8/2008 |
| WO | WO2009/114934 A1 | 9/2009 |

OTHER PUBLICATIONS

Sahni et al., "Electromagnetic Heating Methods for Heavy Oil Reservoirs." 2000 Society of Petroleum Engineers SPE/AAPG Western Regional Meeting, Jun. 19-23, 2000.

Power et al., "Froth Treatment: Past, Present & Future." Oil Sands Symposium, University of Alberta, May 3-5, 2004.

Flint, "Bitumen Recovery Technology A Review of Long Term R&D Opportunities." Jan. 31, 2005. LENEF Consulting (1994) Limited.

"Froth Flotation." Wikipedia, the free encyclopedia. Retrieved from the internet from: http://en.wikipedia.org/wiki/Froth_flotation, Apr. 7, 2009.

"Relative static permittivity," Wikipedia, the free encyclopedia, Retrieved from the Internet from http://en.wikipedia.org/w/index/php?title=Relative_static_permittivity&printable=yes, Feb. 12, 2009.

"Tailings." Wikipedia, the free encyclopedia, Retrieved from the Internet from http://en.wikipedia.org/w/index.php?title=Tailings&printable=yes, Feb. 12, 2009.

PCT International Search Report and Written Opinion in PCT/US2010/025765, Jun. 30, 2010.

PCT International Search Report and Written Opinion in PCT/US2010/025772, Aug. 9, 2010.

PCT International Search Report and Written Opinion in PCT/US2010/025763, Jun. 4, 2010.

PCT International Search Report and Written Opinion in PCT/US2010/025807, Jun. 17, 2010.
PCT International Search Report and Written Opinion in PCT/US2010/025804, Jun. 30, 2010.
PCt International Search Report and Written Opinion in PCT/US2010/025769, Jun. 10, 2010.
A. Godio: "Open ended-coaxial Cable Measurements of Saturated Sandy Soils", American Journal of Environmental Sciences, vol. 3, No. 3, 2007, pp. 175-182, XP002583544.
U.S. Appl. No. 12/886,338, filed Sep. 20, 2010 (unpublished).
Butler, R.M. "Theoretical Studies on the Gravity Drainage of Heavy Oil During In-Situ Steam Heating", Can J. Chem Eng, vol. 59, 1981.
Butler, R. and Mokrys, I., "A New Process (VAPEX) for Recovering Heavy Oils Using Hot Water and Hydrocarbon Vapour", Journal of Canadian Petroleum Technology, 30(1), 97-106, 1991.
Butler, R. and Mokrys, I., "Recovery of Heavy Oils Using Vaporized Hydrocarbon Solvents: Further Development of the VAPEX Process", Journal of Canadian Petroleum Technology, 32(6), 56-62, 1993.
Butler, R. and Mokrys, I., "Closed Loop Extraction Method for the Recovery of Heavy Oils and Bitumens Underlain by Aquifers: the VAPEX Process", Journal of Canadian Petroleum Technology, 37(4), 41-50, 1998.
Das, S.K. and Butler, R.M., "Extraction of Heavy Oil and Bitumen Using Solvents at Reservoir Pressure" CIM 95-118, presented at the CIM 1995 Annual Technical Conference in Calgary, Jun. 1995.
Das, S.K. and Butler, R.M., "Diffusion Coefficients of Propane and Butane in Peace River Bitumen" Canadian Journal of Chemical Engineering, 74, 988-989, Dec. 1996.
Das, S.K. and Butler, R.M., "Mechanism of the Vapour Extraction Process for Heavy Oil and Bitumen", Journal of Petroleum Science and Engineering, 21, 43-59, 1998.
Dunn, S.G., Nenniger, E. and Rajan. R., "A Study of Bitumen Recovery by Gravity Drainage Using Low Temperature Soluble Gas Injection", Canadian Journal of Chemical Engineering, 67, 978-991, Dec. 1989.
Frauenfeld, T., Lillico, D., Jossy, C., Vilcsak, G., Rabeeh, S. and Singh, S., "Evaluation of Partially Miscible Processes for Alberta Heavy Oil Reservoirs", Journal of Canadian Petroleum Technology, 37(4), 17-24, 1998.
Mokrys, I., and Butler, R., "In Situ Upgrading of Heavy Oils and Bitumen by Propane Deasphalting: The VAPEX Process", SPE 25452, presented at the SPE Production Operations Symposium held in Oklahoma City OK USA, Mar. 21-23, 1993.
Nenniger, J.E. and Dunn, S.G., "How Fast is Solvent Based Gravity Drainage?", CIPC 2008-139, presented at the Canadian International Petroleum Conference, held in Calgary, Alberta Canada, Jun. 17-19, 2008.
Nenniger, J.E. and Gunnewick, L., "Dew Point vs. Bubble Point: A Misunderstood Constraint on Gravity Drainage Processes", CIPC 2009-065, presented at the Canadian International Petroleum Conference, held in Calgary, Alberta Canada, Jun. 16-18, 2009.
Bridges, J.E., Sresty, G.C., Spencer, H.L. and Wattenbarger, R.A., "Electromagnetic Stimulation of Heavy Oil Wells", 1221-1232, Third International Conference on Heavy Oil Crude and Tar Sands, UNITAR/UNDP, Long Beach California, USA Jul. 22-31, 1985.
Carrizales, M.A., Lake, L.W. and Johns, R.T., "Production Improvement of Heavy Oil Recovery by Using Eectromagnetic Heating", SPE115723, presented at the 2008 SPE Annual Technical Conference and Exhibition held in Denver, Colorado, USA, Sep. 21-24, 2008.
Carrizales, M. and Lake, L.W., "Two-Dimensional COMSOL Simulation of Heavy-Oil Recovery by Electromagnetic Heating", Proceedings of the COMSOL Conference Boston, 2009.
Chakma, A. and Jha, K.N., "Heavy-Oil Recovery from Thin Pay Zones by Electromagnetic Heating", SPE24817, presented at the 67th Annual Technical Conference and Exhibition of the Society of Petroleum Engineers held in Washington, DC, Oct. 4-7, 1992.
Chhetri, A.B. and Islam, M.R., "A Critical Review of Electromagnetic Heating for Enhanced Oil Recovery", Petroleum Science and Technology, 26(14), 1619-1631, 2008.

Chute, F.S., Vermeulen, F.E., Cervenan, M.R. and McVea, F.J., "Electrical Properties of Athabasca Oil Sands", Canadian Journal of Earth Science, 16, 2009-2021, 1979.
Davidson, R.J., "Electromagnetic Stimulation of Lloydminster Heavy Oil Reservoirs", Journal of Canadian Petroleum Technology, 34(4), 15-24, 1995.
Hu, Y., Jha, K.N. and Chakma, A., "Heavy-Oil Recovery from Thin Pay Zones by Electromagnetic Heating", Energy Sources, 21(1-2), 63-73, 1999.
Kasevich, R.S., Price, S.L., Faust, D.L. and Fontaine, M.F., "Pilot Testing of a Radio Frequency Heating System for Enhanced Oil Recovery from Diatomaceous Earth", SPE28619, presented at the SPE 69th Annual Technical Conference and Exhibition held in New Orleans LA, USA, Sep. 25-28, 1994.
Koolman, M., Huber, N., Diehl, D. and Wacker, B., "Electromagnetic Heating Method to Improve Steam Assisted Gravity Drainage", SPE117481, presented at the 2008 SPE International Thermal Operations and Heavy Oil Symposium held in Calgary, Alberta, Canada, Oct. 20-23, 2008.
Kovaleva, L.A., Nasyrov, N.M. and Khaidar, A.M., Mathematical Modelling of High-Frequency Electromagnetic Heating of the Bottom-Hole Area of Horizontal Oil Wells, Journal of Engineering Physics and Thermophysics, 77(6), 1184-1191, 2004.
McGee. B.C.W. and Donaldson, R.D., "Heat Transfer Fundamentals for Electro-thermal Heating of Oil Reservoirs", CIPC 2009-024, presented at the Canadian International Petroleum Conference, held in Calgary, Alberta, Canada Jun. 16-18, 2009.
Ovalles, C., Fonseca, A., Lara, A., Alvarado, V., Urrecheaga, K., Ranson, A. and Mendoza, H., "Opportunities of Downhole Dielectric Heating in Venezuela: Three Case Studies Involving Medium, Heavy and Extra-Heavy Crude Oil Reservoirs" SPE78980, presented at the 2002 SPE International Thermal Operations and Heavy Oil Symposium and International Horizontal Well Technology Conference held in Calgary, Alberta, Canada, Nov. 4-7, 2002.
Rice, S.A., Kole A.L. and Neate, C.J., "A Test of the Electric Heating Process as a Means of Stimulating the Productivity of an Oil Well in the Schoonebeek Field", CIM 92-04 presented at the CIM 1992 Annual Technical Conference in Calgary, Jun. 7-10, 1992.
Sahni, A. and Kumar, M. "Electromagnetic Heating Methods for Heavy Oil Reservoirs", SPE62550, presented at the 2000 SPE/AAPG Western Regional Meeting held in Long Beach, California, Jun. 19-23, 2000.
Sayakhov, F.L., Kovaleva, L.A. and Nasyrov, N.M., "Special Features of Heat and Mass Exchange in the Face Zone of Boreholes upon Injection of a Solvent with a Simultaneous Electromagnetic Effect", Journal of Engineering Physics and Thermophysics, 71(1), 181-165, 1998.
Spencer, H.L., Bennett, K.A. and Bridges, J.E. "Application of the IITRI/Uentech Electromagnetic Stimulation Process to Canadian Heavy Oil Reservoirs" Paper 42, Fourth International Conference on Heavy Oil Crude and Tar Sands, UNITAR/UNDP, Edmonton, Alberta, Canada, Aug. 7-12, 1988.
Sresty, G.C., Dev, H., Snow, R.H. and Bridges, J.E., "Recovery of Bitumen from Tar Sand Deposits with the Radio Frequency Process", SPE Reservoir Engineering, 85-94, Jan. 1986.
Vermulen, F. and McGee, B.C.W., "In Situ Electromagnetic Heating for Hydrocarbon Recovery and Environmental Remediation", Journal of Canadian Petroleum Technology, Distinguished Author Series, 39(8), 25-29, 2000.
Schelkunoff, S.K. and Frits, H.T., "Antennas: Theory and Practice", John Wiley & Sons, Inc., London, Chapman Hall, Limited, pp. 229-244, 351-353, 1952.
Gupta, S.C., Gittins, S.D., "Effect of Solvent Sequencing and Other Enhancement on Solvent Aided Process", Journal of Canadian Petroleum Technology, vol. 46, No. 9, pp. 57-61, Sep. 2007.
PCT Notification of Transmittal of the International Search Report and The Written Opinion of the International Searching Authority, or the Declaration, in PCT/US2010/025761, dated Feb. 9, 2011.
PCT Notification of Transmittal of the International Search Report and The Written Opinion of the International Searching Authonty, or the Declaration, in PCT/US2010/057090, dated Mar. 3, 2011.

"Control of Hazardous Air Pollutants From Mobile Sources", U.S. Environmental Protection Agency, Mar. 29, 2006. p. 15853 (http://www.epa.gov/EPA-AIR/2006/March/Day-29/a2315b.htm).

Von Hippel, Arthur R., Dielectrics and Waves, Copyright 1954, Library of Congress Catalog Card No. 54-11020, Contents, pp. xi-xii; Chapter II, Section 17, "Polyatomic Molecules", pp. 150-155; Appendix C-E, pp. 273-277, New York, John Wiley and Sons.

United States Patent and Trademark Office, Non-final Office action issued in U.S. Appl. No. 12/396,247, dated Mar. 28, 2011.

United States Patent and Trademark Office, Non-final Office action issued in U.S. Appl. No. 12/396,284, dated Apr. 26, 2011.

Patent Cooperation Treaty, Notification of Transmittal of the International Search Report and The Written Opinion of the International Searching Authority, or the Declaration, in PCT/US2010/025808, dated Apr. 5, 2011.

Deutsch, C.V., McLennan, J.A., "The Steam Assisted Gravity Drainage (SAGD) Process," Guide to SAGD (Steam Assisted Gravity Drainage) Reservoir Characterization Using Geostatistics, Centre for Computational Statistics (CCG), Guidebook Series, 2005, vol. 3; p. 2, section 1.2, published by Centre for Computational Statistics, Edmonton, AB, Canada, Copy right 2005.

Marcuvitz, Nathan, Waveguide Handbook; 1986: Institution of Engineering and Technology, vol. 21 of IEE Electromagnetic Wave series, ISBN 0863410588, Chapter 1, pp. 1-54, published by Peter Peregrinus Ltd. on behalf of The Institution of Electrical Engineers, © 1986.

Marcuvitz, Nathan, Waveguide Handbook; 1966: Institution of Engineering and Technology, vol. 21 of IEE Electromagnetic Wave series, ISBN 0863410588, Chapter 2.3, pp. 66-72, published by Peter Peregrinus Ltd. on behalf of The Institution of Electrical Engineers, © 1986.

Carlson et al., "Development of the I IT Research Institute RF Heating Process for In Situ Oil Shale/Tar Sand Fuel Extraction—An Overview", Apr. 1981.

"Technologies for Enhanced Energy Recovery" Executive Summary, Radio Frequency Dielectric Heating Technologies for Conventional and Non-Conventional Hydrocarbon-Bearing Formulations, Quasar Energy, LLC, Sep. 3, 2009, pp. 1-6.

Burnhan, "Slow Radio-Frequency Processing of Large Oil Shale Volumes to Produce Petroleum-like Shale Oil," U.S. Department of Energy, Lawrence Livermore National Laboratory, Aug. 20, 2003, UCRL-ID-155045.

Sahni et al., "Electromagnetic Heating Methods for Heavy Oil Reservoirs," U.S. Department of Energy, Lawrence Livermore National Laboratory, May 1, 2000, UCL-JC-138802.

Abernethy, "Production Increase of Heavy Oils by Electromagnetic Heating," The Journal of Canadian Petroleum, Technology, Jul.-Sep. 1976, pp. 91-97.

Sweeney, et al., "Study of Dielectric Properties of Dry and Saturated Green River Oil Shale," Lawrence Livermore National Laboratory, Mar. 26, 2007, revised manuscript Jun. 29, 2007, published on Web Aug. 25, 2007.

Kinzer, "Past, Present, and Pending Intellectual Property for Electromagnetic Heating of Oil Shale," Quasar Energy LLC, 28th Oil Shale Symposium Colorado School of Mines, Oct. 13-15, 2008. pp. 1-18.

Kinzer, "Past, Present, and Pending Intellectual Property for Electromagnetic Heating of Oil Shale," Quasar Energy LLC, 28th Oil Shale Symposium Colorado School of Mines, Oct. 13-15, 2008, pp. 1-33.

Kinzer, A Review of Notable Intellectual Property for In Situ Electromagnetic Heating of Oil Shale, Quasar Energy LLC, Ref. 2007.

* cited by examiner

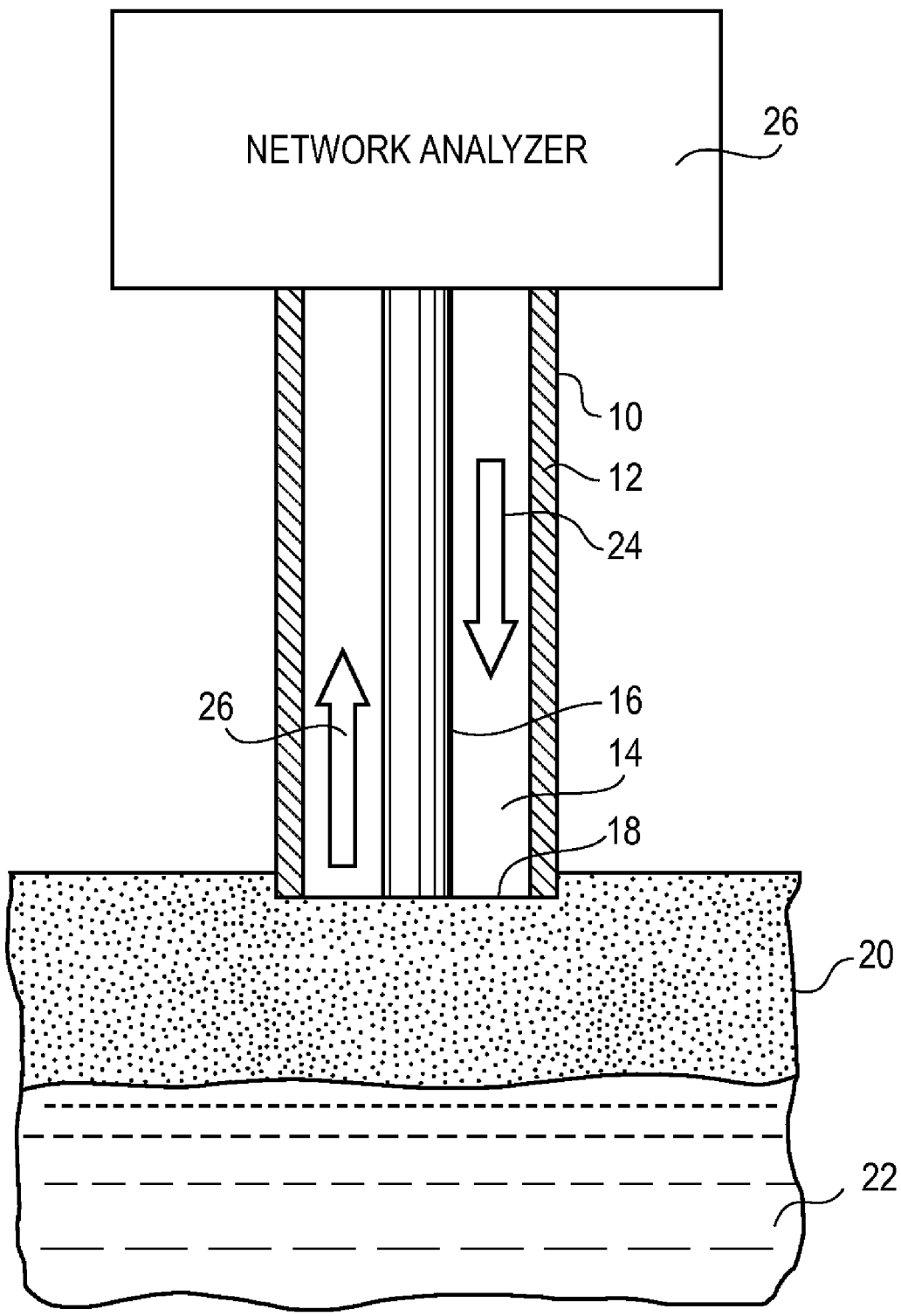

DIELECTRIC CHARACTERIZATION OF BITUMINOUS FROTH

CROSS REFERENCE TO RELATED APPLICATIONS

This specification is related to McAndrews, Held & Malloy Serial Numbers:
Ser. No. 12/396,247
Ser. No. 12/395,995
Ser. No. 12/395,945
Ser. No. 12/396,192
Ser. No. 12/396,021
Ser. No. 12/396,284
Ser. No. 12/396,057
Ser. No. 12/395,918
filed on the same date as this specification, each of which is incorporated by reference herein

STATEMENT REGARDING FEDERALLY SPONSORED RESEARCH OR DEVELOPMENT

[Not Applicable]

BACKGROUND OF THE INVENTION

The invention concerns the dielectric characterization of a substance to be heated, and more particularly to a method of heating the substance by the application of radio-frequency (RF) energy.

The current state-of-the-art suggests that heating bituminous froth is a desired step in the hydrocarbon recovery process. However this implementation has been proposed with direct steam which results in the dilution of the froth and corrupts its chemical composition and value.

Bituminous froth is unstable and loses its physical characteristics when handled. In the manufacturing process, its exact position and surface face-orientation is not accurately known. As a result, determining its dielectric characteristics is difficult. No prior record appears to exist on the resolution of this problem Water is used and reused in the combined extraction, froth treatment, and tailings handling in present processes.

In addition, the insertion of steam into the froth at this point requires that the precipitated water be removed from the froth before the next step in the process (the up-grader) and that this water be either chemically scrubbed (cleaned) if to be discharged or, if to be reintroduced into the process, be reheated.

The use of a secondary applicator, like a heat exchanger, is not believed to be useful due to the chemical nature of the froth. Such an implementation results in an excessive build up of undesired materials on the applicator.

No major alternatives to the water-based bitumen extraction are forecasted to emerge in the next decade.

A key challenge to the water based extraction process in future will be water and solids management.

Alternatives for processing the whole ore, such as solvent based extraction, have had decades of development, but have failed to overcome the basic losses (of solvent or energy) in the large mass of sand that has to be processed. Consequently, most research and technology development in mining is aimed at sustaining and improving the integration of mining operations with water-based extraction.

Bituminous froth, consisting approximately of 60% bitumen, 30% water, and 10% solids in a bubbly froth, is unstable (with time and material handling). This fact exacerbates the difficulties encountered with traditional measurement methodology.

SUMMARY OF THE INVENTION

An aspect of the invention concerns a method of determining the permittivity of a substance, e.g., a bituminous froth, using a probe comprising inner and outer conductors separated by a dielectric material of known permittivity, the probe having an at least generally planar end surface normal to the axis of the probe. A signal source and a signal receiver are operatively connected to the probe. In this aspect, the method can be carried out by contacting the substance with the planar end surface of the probe to form an interface between the probe and the substance, such as froth. The method further involves measuring the reflection coefficient of the substance by (1) transmitting a signal through the probe to the interface, (2) receiving the signal reflected from the interface, and (3) comparing said transmitted and reflected signals, and then calculating the permittivity of said substance from the reflection coefficient as so measured.

Another aspect of the invention concerns a method of heating a substance, such as bituminous froth, by determining the permittivity of the substance, e.g., a bituminous froth, using a probe, a signal source, and a signal receiver as described above. In this aspect, the determination of the permittivity is carried out by contacting the substance with the planar end surface of said probe to form an interface between the probe and the substance, such as the froth. The determination further involves measuring the reflection coefficient of the substance by (1) transmitting a signal through the probe to the interface, (2) receiving the signal reflected from the interface, and (3) comparing said transmitted and reflected signals, and then calculating the permittivity of said substance from the reflection coefficient as so measured. The method further involves providing a radiation source physically and electrically spaced from the substance.

BRIEF DESCRIPTION OF THE DRAWINGS

FIG. 1 is a diagrammatic view of an embodiment of the probe, illustrating practice of an embodiment of the method.

DETAILED DESCRIPTION OF THE PREFERRED EMBODIMENTS

The present invention will now be described more fully hereinafter with reference to the accompanying drawings, in which one or more embodiments of the invention are shown. This invention may, however, be embodied in many different forms and should not be construed as limited to the embodiments set forth herein. Rather, these embodiments are examples of the invention, which has the full scope indicated by the language of the claims. Like numbers refer to like elements throughout.

It is reported in the literature that 8% of the bitumen entering the extraction and froth treatment steps today is lost to tailings, and the value of just half of that loss in terms of the energy reduction is estimated at some $250 million annually for every million barrels of actual production. See, Flint, Len, "Bitumen Recovery Technology" p. 40 (April 2005). Improving froth treatment is viewed in the literature as a high value target. See Flint, pp. 53-59.

Electromagnetically heating the froth could reduce water demands.

Heating bituminous froth as it is produced with RF can improve processing throughput and reduce cost.

The application of RF heat to the bituminous froth can be performed remotely without contacting the substance (the froth) itself.

Efficient RF heating requires radiation at wavelengths that penetrate the material and generate heat within it.

The process of conveying RF energy (or radiating) into a material is dictated by the dielectric characteristics of the material in question and by the electrical characteristics of the source.

Thus, the electromagnetic characterization of the various materials to be heated is an important aspect of an RF heating approach.

Determining the dielectric characteristics of bituminous froth has previously been a difficult proposition to accomplish. The present inventors contemplate that the difficulty has resulted because the location and orientation of the froth sample relative to the test probe must be precisely known in order to obtain an accurate result.

In one aspect, the measurement is carried out by placing the material in-question in contact with a controlled sampling device such as a coaxial chamber.

By characterizing the dielectric properties of the froth, it is possible to apply heat to the froth exclusively and efficiently. This can be accomplished by accurately characterizing the permittivity and the permeability of the froth itself without disturbing its state.

Such a process is facilitated when the material is addressed in such a way that its position and orientation relative to the test instrument probe is precisely known.

The process of characterizing bituminous froth requires that the material (the froth) be minimally disturbed so its dielectric characteristics can be determined as it sits in the state to which the RF energy is to be applied.

As noted, an aspect of the invention concerns a method of determining the permittivity of a substance, e.g., a bituminous froth. The determination may be made utilizing a probe, such as coaxial probe 10 depicted in FIG. 1, in which an outer conductor 12 encloses a dielectric material 14 having a known permittivity and an inner conductor 16. The probe 10 has a planar end surface 18 normal to the axis of the probe. The planar end surface 18 may be polished to increase the precision of the measurement. In this aspect, the method is carried out by contacting the substance 20, in this instance bitumen froth with unknown permittivity floating on a middling slurry 22 from which the bitumen froth 20 has separated during processing. The bitumen froth 20 is contacted with the planar end surface 18 of the probe 10 to form an interface between the probe and the froth 20. The planar end surface 18 of the probe 10 therefore functions as a reference plane for the permittivity determination.

Because the impedance of the froth or other substance will, in most circumstances, differ from that of the dielectric material of the probe, a portion of the signal 24 directed at the interface 18 will be reflected rather than propagated into the froth.

The method further involves measuring the reflection coefficient of the substance by (1) transmitting a signal 24 through the probe to the interface, (2) receiving the signal 26 reflected from the interface, (3) comparing said transmitted and reflected signals, all by use of the network analyzer 26 as is known in the art. One can then calculate the permittivity of the substance from the reflection coefficient as so measured.

In general, the permittivity $\in_r$ of the substance (here, the froth) is determined by the following formula:

$$\varepsilon_r = \frac{c^2}{\omega^2} \cdot \left[ \left( \frac{z+1}{z-1} \right)^2 + \left( \frac{2\pi}{\lambda_c} \right)^2 \right]$$

wherein,
c=speed of light
$\omega$=frequency of the transmitted signal
$\lambda_c$=wavelength of the transmitted signal
and z is determined as follows:

$$z = \frac{\Gamma+1}{\Gamma-1}$$

wherein
$\Gamma$=reflection coefficient

Once the electromagnetic properties of the target material have been characterized, the next step is to select a radiation source.

Maximum energy efficiency is achieved when the impedance of the radiating source matches the complex conjugate of the impedance of the material to be heated. Otherwise, excessive energy is reflected from the material interface and the energy is wasted.

Selection of the proper wavelength and design of the radiating source to match the impedance of the material requires knowledge of both the real and imaginary components of permittivity and its dependence on frequency. The dielectric characteristics of the material dictate its impedance and drive the design of the transmitter interface. The real and imaginary components of the dielectric properties of the material determine the material impedance, which is a complex number.

Other constituent materials, like water or solids for instance, can be extracted (not required), or even simply excluded (nor included) from the heating process. This is simply a consequence of the fact that the driving mechanism impedance dictates what element of the load is dissipating this RF energy.

This approach permits the application of heat only to the element of the system of interest and not to other constituents, thus improving efficiency. This approach further may provide uniform heating, which, in turn, increases process yield. This approach further may permit the heating process to occur remotely and with minimal operator intervention. By heating the froth remotely, (i.e. by irradiation), the froth does not have to be physically contacted by any heating equipment. This is especially advantageous because of the physical characteristics of the froth—it is very viscous and tends to "gum up" whatever it passes through. This allows the froth to be heated while being transported using known mechanical handling means that work. This avoids the need for operator intervention and avoids interruptions in plant operation caused by froth transport failures.

We claim:
1. A method of determining a permittivity of a hydrocarbon resource comprising:
    physically contacting the hydrocarbon resource with a planar end surface of a probe to define an interface;
    measuring a reflection coefficient of the hydrocarbon resource by at least
        transmitting a signal through the probe to the interface,
        receiving a reflected signal from the interface,
        comparing the transmitted and reflected signals; and
    calculating the permittivity of the hydrocarbon resource based upon the reflection coefficient.

2. The method according to claim 1, wherein the hydrocarbon resource comprises bituminous froth.

3. The method according to claim 1, wherein physically contacting the hydrocarbon resource with the planar end surface of the probe comprises physically contacting the hydrocarbon resource with a planar end surface of a probe having an outer conductor, an inner conductor and a dielectric material therebetween.

4. The method according to claim 1, wherein the probe has an axis along a length thereof; and wherein physically contacting the hydrocarbon resource with the planar end surface of the probe comprises physically contacting the hydrocarbon resource with a planar end surface normal to the axis.

5. The method according to claim 1, wherein the signal transmitted through the probe to the interface is transmitted from a signal source coupled to the probe.

6. The method according to claim 1, wherein the reflected signal from the interface is received by a signal receiver coupled to the probe.

7. A method of heating a hydrocarbon resource sample comprising:
   physically contacting the hydrocarbon resource sample with a planar end surface of a probe to define an interface;
   measuring a reflection coefficient of the hydrocarbon resource sample by at least
      transmitting a signal through the probe to the interface,
      receiving a reflected signal from the interface, and
      comparing the transmitted and reflected signals;
   calculating the permittivity of the hydrocarbon resource sample based upon the reflection coefficient;
   calculating an impedance of the hydrocarbon resource sample from the calculated permittivity; and
   applying radio frequency (RF) energy from an RF source to the hydrocarbon resource sample, the RF source having a source impedance corresponding to the impedance of the hydrocarbon resource sample.

8. The method according to claim 7, wherein the hydrocarbon resource sample comprises a bituminous froth sample.

9. The method according to claim 7, wherein providing the probe comprises providing a probe having an outer conductor, an inner conductor, and a dielectric material therebetween.

10. The method according to claim 7, wherein the probe has an axis along a length thereof; and wherein physically contacting the hydrocarbon resource with the planar end surface of the probe comprises physically contacting the hydrocarbon resource with a planar end surface normal to the axis.

11. The method according to claim 7, wherein the signal transmitted through the probe to the interface is transmitted from a signal source coupled to the probe.

12. The method according to claim 7, wherein the reflected signal from the interface is received by a signal receiver coupled to the probe.

13. The method according to claim 7, further comprising acquiring the hydrocarbon resource sample.

* * * * *